(12) United States Patent
Henderson

(10) Patent No.: US 10,908,142 B2
(45) Date of Patent: Feb. 2, 2021

(54) MEASURING TOTAL ORGANIC CONTENT OF SOURCE ROCK

(71) Applicant: Saudi Arabian Oil Company, Dhahran (SA)

(72) Inventor: Sebastian Robert Glynn Henderson, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 72 days.

(21) Appl. No.: 16/262,404

(22) Filed: Jan. 30, 2019

(65) Prior Publication Data

US 2020/0240972 A1    Jul. 30, 2020

(51) Int. Cl.
*G01N 1/44*     (2006.01)
*G01N 33/24*    (2006.01)
*G01N 21/61*    (2006.01)

(52) U.S. Cl.
CPC .............. *G01N 33/241* (2013.01); *G01N 1/44* (2013.01); *G01N 21/61* (2013.01)

(58) Field of Classification Search
CPC ....... H01L 2924/00; H01L 2924/13091; H01L 2224/48091; H01L 2924/01015; H01L 2924/01047; H01L 2924/1305; H01L 2924/1461; H01L 2924/181; H01L 2924/30107; H01L 2924/3011; H01L 2924/3025; G01N 33/24; G01N 25/00; G01N 31/12; G01N 33/241; G01N 2030/8854; G01N 30/68; G01N 30/88; G01N 31/005; G01N 33/1846; G01N 33/182; G01N 2001/2893; G01N 27/07; G01N 33/0009; G01N 33/0075; G01N 1/08; G01N 2001/002; G01N 2001/4033; G01N 21/3103; G01N 21/3577; G01N 21/65; G01N 2800/2821; G01N 33/6896;

(Continued)

(56) References Cited

U.S. PATENT DOCUMENTS

| 5,811,308 A | 9/1998 | Espitalie et al. |
| 8,796,035 B2 * | 8/2014 | Espitalie ................ G01N 33/24 |
| | | 436/122 |
| 2013/0125673 A1 * | 5/2013 | Kanipayor ............... G01N 1/42 |
| | | 73/863.11 |

FOREIGN PATENT DOCUMENTS

WO    2015084784    6/2015

OTHER PUBLICATIONS

Carvajal-Ortiz and Gentzis, "Critial considerations when assessing hydrocarbon plays using Rock-Eval pyrolysis and organic petrology data: Data quality revisited," International Journal of Coal Geology, vol. 152, Part A, Nov. 1, 2015, 10 pages.

Lafargue et al., "Rock-Eval 6 Applications in Hydrocarbon Exploration, Production and in Soil Contamination Studies," in Revue de l'Institut Francais de Petrole, vol. 53, No. 4, Oil and Gas Science and Technology 53(4), Jul. 1998, 23 pages.

Fujine, "Source Rock (SR) Analyzer: User Guide," International Ocean Discovery Program, May 12, 2008, 18 pages.

Weatherford Laboratories, "Source Rock Analyzer," Weatherford 2012, 8 pages.

(Continued)

*Primary Examiner* — Irakli Kiknadze
(74) *Attorney, Agent, or Firm* — Fish & Richardson P.C.

(57) ABSTRACT

A stream including oxygen is provided to a rock sample from a subterranean zone. The rock sample is subjected to a first heating process to thermally oxidize at least a portion of the contaminant present in the rock sample. A first level of total organic content (TOC) of the rock sample is determined based on the first heating process. The rock sample is subjected to a second heating process to thermally oxidize at least a portion of the organic material present in the rock sample. A second level of TOC of the rock sample is determined based on the second heating process.

19 Claims, 10 Drawing Sheets

(58) Field of Classification Search
CPC .... G01N 21/21; G01N 21/3581; G01N 21/59; G01N 21/6486; G01N 2333/4709; G01N 33/483; G01N 33/487; G01N 1/24; G01N 2015/1043; G01N 21/17; G01N 1/44; G01N 1/10; G01N 1/4022; G01N 1/4044; G01N 1/42; G01N 21/61; E21B 49/02; Y10T 436/18; Y10T 436/182; Y10T 436/184; Y10T 436/186; Y10T 436/188; Y10T 436/204998; B01L 2300/049; B01L 2300/0832; B01L 2300/1822; B01L 2300/1838; B01L 2300/1872; B01L 2300/1883; B01L 2300/1894; B01L 3/04; B01L 7/00
USPC ........................................................ 250/255
See application file for complete search history.

(56) References Cited

OTHER PUBLICATIONS

Behar et al., "Rock-eval 6 Technology: Performances and Developments," Oil & Gas Science and Technology, Mar. 2001, 56(2): 111-134.

Sedat et al., "Oxidation max: A new thermal maturity indicator for hydrocarbon source rocks," Organic Chemistry, Aug. 2017, 113: 254-261.

PCT International Search Report and Written Opinion in International Appln. No. PCT/US2020/015330, dated Jun. 6, 2020, 16 pages.

\* cited by examiner

MEASURING TOTAL ORGANIC CONTENT OF SOURCE ROCK

TECHNICAL FIELD

This disclosure relates to measuring total organic content of source rocks.

BACKGROUND

Commercial-scale hydrocarbon extraction from source rocks and reservoirs can require significant capital. It is therefore beneficial to obtain as much accurate data as possible about a formation in order to assess its commercial viability and subsequently to optimize cost and design of development. Organic petrological and geochemical investigations are examples of suitable methods to obtain data. Accurately measuring total organic content (TOC) of source rocks that have been contaminated, for example, by exposure to oil based mud during drilling operations, can present a challenge.

SUMMARY

This disclosure describes technologies relating to measuring total organic content of source rocks.

Certain aspects of the subject matter described can be implemented as a method. A stream including oxygen is provided to a rock sample from a subterranean zone. The rock sample includes organic material and a contaminant to which the rock sample was exposed during a drilling operation in the subterranean zone. While providing the stream to the rock sample, the rock sample is subjected to a first heating process to thermally oxidize at least a portion of the contaminant and generate a first amount of carbon oxide. The first heating process includes heating the rock sample to a first temperature greater than 320 degrees Celsius (° C.) and maintaining the rock sample at the first temperature for a first time duration. While providing the stream to the rock sample, the rock sample is subjected to a second heating process to thermally oxidize at least a portion of the organic material and generate a second amount of carbon dioxide. The second heating process includes heating the rock sample to a second temperature greater than 360° C. and maintaining the rock sample at the second temperature for a second time duration. The second temperature is different from the first temperature. A first level of total organic content (TOC) of the rock sample is determined based on the first amount of generated carbon oxide resulting from subjecting the rock sample to the first heating process. A second level of TOC of the rock sample is determined based on the second amount of generated carbon oxide resulting from subjecting the rock sample to the second heating process.

This, and other aspects, can include one or more of the following features.

The rock sample can be heated to approximately 320° C. before subjecting the rock sample to the first heating process.

The first temperature can be approximately 360° C., and the first time duration can be approximately 2 minutes.

The second temperature can be approximately 600° C., and the second time duration can be approximately 75 seconds.

Heating the rock sample to the first temperature can include heating the rock sample such that the temperature of the rock sample increases at a rate of approximately 15° C. per minute.

Heating the rock sample to the second temperature can include heating the rock sample such that the temperature of the rock sample increases at a rate of approximately 50° C. per minute.

The rock sample can be ground before providing the stream to the rock sample.

Grinding the rock sample can include grinding the rock sample such that the resulting ground rock sample has an average particle size of at most 250 micrometers.

A portion of the ground rock sample can be reserved before providing the stream to a remaining portion of the ground rock sample. The reserved portion of the ground rock sample can be separated into a first portion and a second portion. A TOC of the first portion can be determined. At least a portion of the contaminant can be removed from the second portion with a solvent. After removing the contaminant from the second portion, a TOC of the second portion can be determined.

The accuracy of the determination of the first and second levels of TOC can be verified. The TOC of the first portion can be compared to a sum of the first level of TOC and the second level of TOC. The TOC of the second portion can be compared to the second level of TOC.

Determining the first level of TOC of the rock sample can include measuring the first amount of generated carbon oxide. Determining the second level of TOC of the rock sample can include measuring the second amount of generated carbon oxide.

Providing the stream to the rock sample can include providing oxygen at a rate of approximately 720 milliliters per minute to the rock sample.

The stream can include at least 99% by volume of oxygen.

Certain aspects of the subject matter described can be implemented as a method. Oxygen is flowed to a rock sample obtained from a subterranean zone. While flowing oxygen to the rock sample, the rock sample is heated to a first temperature to thermally oxidize a first portion of the rock sample, thereby generating a first amount of carbon oxide. While flowing oxygen to the rock sample (and after heating the rock sample to the first temperature), the rock sample is heated to a second temperature greater than the first temperature to thermally oxidize a second portion of the rock sample, thereby generating a second amount of carbon oxide. The first amount of generated carbon oxide is measured to determine a first level of total organic content (TOC) of the rock sample. The second amount of generated carbon oxide is measured to determine a second level of TOC of the rock sample.

This, and other aspects, can include one or more of the following features.

Heating the rock sample to the first temperature includes heating the rock sample such that the temperature of the rock sample increases at a rate of approximately 15° C. per minute until the temperature of the rock sample reaches approximately 360° C.

The rock sample can be maintained at approximately 360° C. for approximately 2 minutes once the temperature of the rock sample reaches approximately 360° C. and before heating the rock sample to the second temperature.

Heating the rock sample to the second temperature can include heating the rock sample such that the temperature of the rock sample increases at a rate of approximately 50° C. per minute until the temperature of the rock sample reaches approximately 600° C.

The rock sample can be maintained at approximately 600° C. for approximately 75 seconds once the temperature of the rock sample reaches approximately 600° C.

Measuring the first and second amounts of generated carbon oxide can include using a nondispersive infrared (NDIR) sensor.

Flowing oxygen to the rock sample can include flowing oxygen to the rock sample at a rate of approximately 720 milliliters per minute.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

Oil based mud can provide benefits in drilling operations, but its use can also complicate analyses and interpretations of geochemical samples. Oil based muds can contaminate rock samples and therefore affect the measurement of total organic content (TOC) of the rock samples. Therefore, traditional methods typically require such rock samples to be pre-processed before analysis. For example, solvent extraction is generally an effective and commonly employed method for removing solvent-soluble organic contaminants from the rock samples. However, solvent extraction can often be expensive, time consuming, and produce large amounts of chemical waste. By implementing the subject matter described in this disclosure, the native TOC of a rock sample (that is, the TOC attributable to the organic content of the rock sample, excluding contaminants) can be measured quickly (for example, within 15 minutes) and accurately, without needing to pre-process the rock sample, which can be time consuming and in some cases introduce contaminants. The methods described can allow for no chemical waste to be produced and can also be applied across various fluid types.

Figure 1:
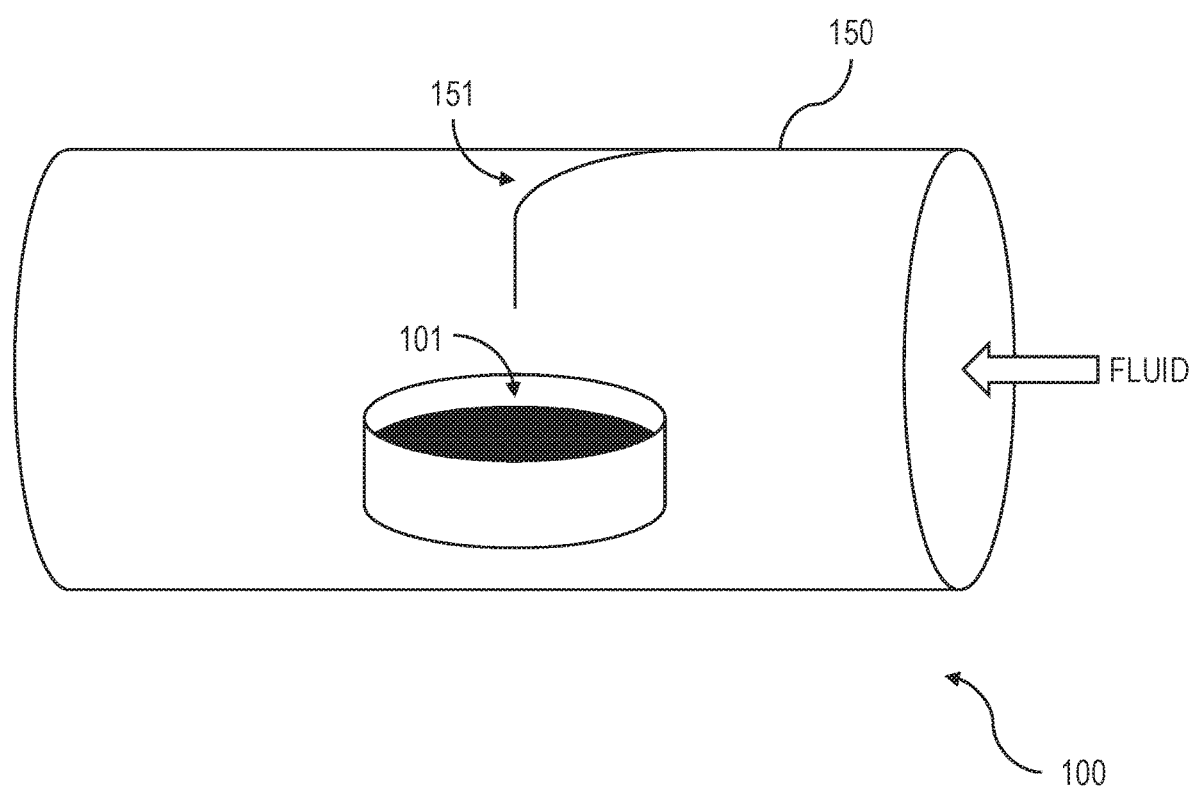
FIG. 1 is a schematic diagram of an example system for determining total organic content (TOC) of a rock sample.

FIG. 1 an example system 100 that can be used to determine a level of TOC of a rock sample 101. The system 100 includes a chamber 150 within which the rock sample 101 can be placed. The chamber 150 is constructed of a material to be able to withstand extreme temperatures, for example, greater than 600 degrees Celsius (° C.). For example, the chamber 150 can be constructed of silica. The chamber 150 can have any shape, for example, a cylindrical tube shape. The chamber 150 can be sealed on one end and allow a flow of fluid (such as oxygen) to enter the chamber 150 at an opposite end. The level of TOC of the rock sample 150 can be determined by providing oxygen and heat to the rock sample 101 while the rock sample 101 is within the chamber 150.

The rock sample 101 can be obtained from a subterranean zone. For example, the rock sample can be obtained from a well that has been drilled into the subterranean zone. In some implementations, the subterranean zone is a formation within the Earth defining a reservoir, but in other instances, the subterranean zone can be multiple formations or a portion of a formation. The subterranean zone can include, for example, a formation, a portion of a formation, or multiple formations in a hydrocarbon-bearing reservoir from which recovery operations can be practiced to recover trapped hydrocarbons. In some implementations, the subterranean zone includes an underground formation of naturally fractured or porous rock containing hydrocarbons (for example, oil, gas, or both). In some implementations, the well can intersect other types of formations, including reservoirs that are not naturally fractured.

Prior to being placed in the chamber 150, the rock sample 101 can be ground or broken into smaller pieces. In this disclosure, the term "grind" should be interpreted in a flexible manner to include any form of reducing a substance into smaller pieces, such as break apart, shear, or pulverize into a powder. In some implementations, the rock sample 101 is ground into powder form such that the ground rock sample 101 can pass through a mesh sieve, for example, a 35-mesh sieve, a 40-mesh sieve, a 45-mesh sieve, a 50-mesh sieve, a 60-mesh sieve, a 70-mesh sieve, an 80-mesh sieve, a 100-mesh sieve, or a 120-mesh sieve. For example, the ground rock sample 101 can have an average particle size of approximately 500 micrometers (µm), approximately 420 µm, approximately 354 µm, approximately 297 µm, approximately 250 µm, approximately 210 µm, approximately 177 µm, approximately 149 µm, or approximately 125 µm. In this disclosure, the terms "approximately" and "about" allow for a deviation of a value of up to 10 percent (%) and any variation from a mentioned value is within the tolerance limits of any machinery used to manufacture the part. In some implementations, approximately 30 milligrams (mg) to approximately 40 mg of the ground rock sample 101 is placed in the chamber 150 for analysis.

Within the chamber 150, the rock sample 101 can be exposed to one or more fluids. For example, an inert gas (such as nitrogen), oxygen, or a combination of these (such as air) can be provided into the chamber 150 while the rock sample 101 is within the chamber 150. The inner volume of the chamber 150 can be heated so that the temperature of the rock sample 101 increases. For example, the chamber 150 can be placed within a furnace. The temperature within the chamber 150 can therefore be adjusted as desired. For example, the temperature of the inner volume of the chamber 150 can adjusted to be in a range of from about 300° C. to about 700° C. The temperature of the inner volume of the chamber 150 can be adjusted at various rates. For example, the furnace can be configured to adjust the temperature of the inner volume of the chamber 150 at approximately 5° C. per minute (° C./min), at approximately 10° C./min, at approximately 15° C./min, at approximately 20° C./min, at approximately 25° C./min, at approximately 30° C./min, at approximately 35° C./min, at approximately 40° C./min, at approximately 45° C./min, at approximately 50° C./min, at approximately 55° C./min, at approximately 60° C./min, at approximately 65° C./min, at approximately 70° C./min, and at approximately 75° C./min. The rate at which the temperature of the inner volume of the chamber 150 is adjusted can be adjusted as desired.

In some implementations, it may be sufficient for the inner volume of the chamber 150 to reach a certain temperature (for example, 360° C.) at a certain temperature increase rate (for example, 15° C./min). In some implementations, the inner volume of the chamber 150 may need to reach a hotter temperature (for example, 380° C.) at a faster temperature increase rate (for example, 20° C./min), so that the material within the chamber 150 (for example, the rock sample 101) reaches a target temperature (for example, 360° C.) at a target temperature increase rate (for example, 15° C./min). Therefore, in some implementations, the temperature within the chamber 150 and the rate at which the temperature is adjusted can be set depending on the material that is being heated in the chamber 150 (for example, the rock sample 101).

The temperature of the rock sample 150 can be measured, for example, by a thermocouple 151. The temperature measuring portion of the thermocouple 151 can be positioned in the vicinity of the rock sample 101 within the chamber 150. For example, the temperature measuring portion of the thermocouple 151 can be positioned approximately 1 centimeter (cm) to approximately 2 cm directly above the rock sample 151 when the sample 150 is positioned within the chamber 150. The temperature within the chamber 150 and the rate at which the temperature is adjusted can be set based on the temperature measured by the thermocouple 151.

Providing oxygen and heat to the rock sample 101 within the chamber 150 can cause the rock sample 101 to thermally oxidize and generate carbon oxide (for example, carbon dioxide and carbon monoxide). A baseline reading of carbon dioxide present within the chamber 150 (not attributable to the thermal oxidation process) can be accounted for and subtracted from the finally measured TOC. The rock sample 101 can undergo a first heating process within the chamber 150 to thermally oxidize any contaminants present in the rock sample 101. The carbon oxide generated during the first heating process can therefore be attributed to the contaminants that were originally present in the rock sample 101. The rock sample 101 can then undergo a second heating process within the chamber 150 to thermally oxidize any remaining organic material in the rock sample 101. The carbon oxide generated during the second heating process can therefore be attributed to the organic content native to the original rock sample 101 (that is, not including the contaminants).

Figure 2:
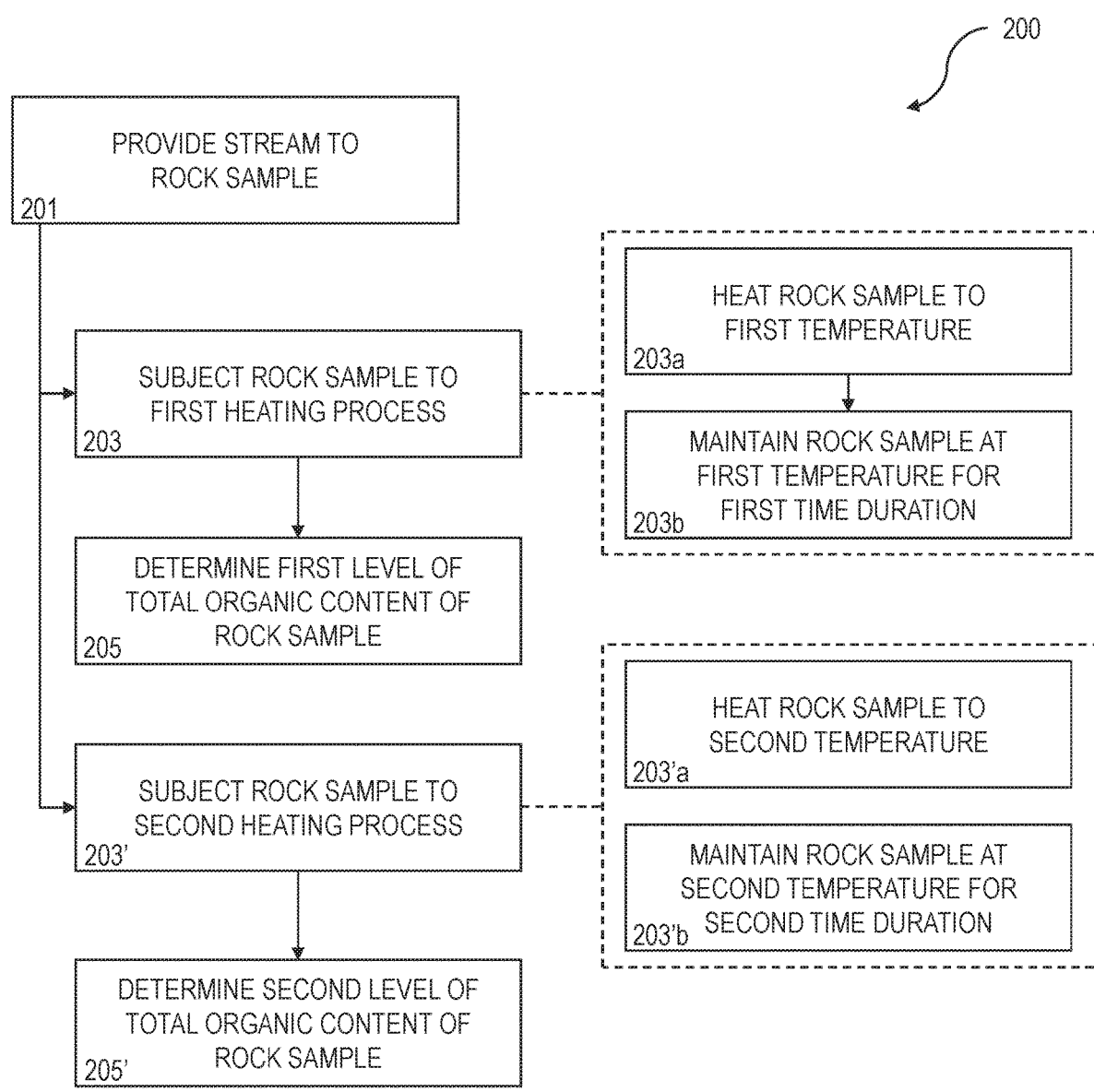
FIG. 2 is a flow chart of an example method for determining TOC of a rock sample.

FIG. 2 is a flow chart of an example method 200 for determining TOC of a rock sample (such as the rock sample 101). The chamber 150 can be used to implement method 200. At step 201, a stream that includes oxygen is provided to the rock sample 101. As mentioned previously, the rock sample 101 is from a subterranean zone. The rock sample 101 can include carbonaceous material (for example, kerogen) and one or more contaminants to which the rock sample 101 was exposed during a drilling operation in the subterranean zone (for example, one or more contaminants from oil based mud). The rock sample 101 can be a ground rock sample 101. As described previously, the rock sample 101 can have, for example, an average particle size of approximately 250 micrometers or smaller. In some implementations, the method 200 includes grinding the rock sample 101 before the stream is provided to the rock sample 101 at step 201. In some implementations, the stream is provided to the rock sample 101 such that oxygen is provided to the rock sample 101 at a rate in a range of from about 700 milliliters per minute (mL/min) to about 750 mL/min (for example, 720 mL/min). In some implementations, the stream is at least 99% by volume of oxygen (for example, approximately 99.5% by volume of oxygen).

While providing the stream to the rock sample 101 at step 201, the rock sample 101 is subjected to a first heating process at step 203 and a second heating process at step 203'. Subjecting the rock sample 101 to the first heating process at step 203 can cause at least a portion of the contaminant to thermally oxidize and generate a first amount of carbon oxide. In other words, the contaminants that are present in the rock sample 101 are thermo-vaporized in the first heating process at step 203. The first heating process includes heating the rock sample 101 to a first temperature that is greater than 320° C. (step 203a) and maintaining the rock sample 101 at the first temperature for a first time duration (step 203b). The first temperature is hot enough and the first time duration is long enough such that approximately all the contaminants (that would have been solvent extracted for traditional methods) are removed from the rock sample 101 at step 203. The first temperature is cool enough and the first time duration is short enough such that breakdown of the native TOC of the rock sample 101 (for example, kerogen maturation or cracking of organic material) is avoided at step 203. In some implementations, the first temperature is in a range of from about 355° C. to about 365° C. (for example, approximately 360° C.). In some implementations, the first time duration is in a range of from about 1 minute to about 10 minutes (for example, approximately 2 minutes). In some implementations, the rock sample 101 is heated to 320° C. before it is heated to the first temperature at step 203a. In some implementations, the rock sample 101 is heated at step 203a such that the temperature of the rock sample 101 (or the inner volume of the chamber 150) increases at a rate in a range of from about 10° C./min to about 30° C./min (for example, approximately 15° C./min).

Subjecting the rock sample 101 to the second heating process at step 203' can cause at least a portion of the organic material to thermally oxidize and generate a second amount of carbon oxide. The second heating process includes heating the rock sample 101 to a second temperature that is greater than 360° C. and different from the first temperature (step 203'a) and maintaining the rock sample 101 at the second temperature for a second time duration (step 203'b). The second temperature is hot enough and the second time duration is long enough such that approximately all the organic carbon content of the rock sample 101 is oxidized at step 203'. The second temperature is cool enough such that oxidation of the inorganic carbon content of the rock sample 101 (for example, carbonate material) is avoided at step 203. In some implementations, the second temperature is in a range of from about 500° C. to about 650° C. (for example, approximately 600° C.). In some implementations, the second time duration is in a range of from about 30 seconds to about 8 minutes (for example, approximately 75 seconds). In some implementations, the rock sample 101 is heated at step 203'a such that the temperature of the rock sample 101 (or the inner volume of the chamber 150) increases at a rate in a range of from about 25° C./min to about 50° C./min. The rock sample 101 can be heated at step 203'a at a temperature increase rate that is slow enough to avoid causing a runaway reaction but fast enough to avoid needlessly prolonging the time duration of step 203'a (for example, approximately 50° C./min).

At step 205, a first level of TOC of the rock sample 101 is determined based on the first amount of generated carbon oxide resulting from subjecting the rock sample 101 to the first heating process at step 203. The first amount of generated carbon oxide can be measured, for example, by using a nondispersive infrared (NDIR) sensor. The NDIR sensor can measure various gases, for example, carbon dioxide and carbon monoxide. The first level of TOC of the rock sample 101 can be attributed to contaminants that were present in the rock sample 101. The first level of TOC of the rock sample 101 can be attributed to organic content which would have been extracted during a pre-processing step associated with traditional methods (for example, solvent extraction). Maintaining the rock sample 101 at the first temperature at step 203b for too short of a time duration may not allow for all of the contaminants to be thermo-vaporized. The rock sample 101 should therefore be maintained at the first temperature at step 203b for enough time to for approximately all of the contaminants to be thermo-vaporized so that the first level of TOC determined at step 205 is acceptably accurate.

At step 205', a second level of TOC of the rock sample 101 is determined based on the second amount of generated carbon oxide resulting from subjecting the rock sample 101 to the second heating process at step 203'. The second amount of generated carbon oxide can be measured, for example, by using the NDIR sensor. The second level of TOC of the rock sample 101 can be attributed to the native organic content that was already present in the rock sample 101 before the rock sample 101 was exposed to the contaminants (for example, during the drilling operations). The second level of TOC of the rock sample 101 can be attributed to organic content that cannot be extracted during a pre-processing step associated with traditional methods (for example, solvent extraction).

In some implementations, it may be desirable to verify the accuracy of the determined levels of TOC of the rock sample 101. In such implementations, a portion of the rock sample 101 can be reserved, and the remaining portion of the rock sample 101 can undergo steps 201, 203, 203', 205, and 205'. The reserved portion of the rock sample 101 can be separated into a first portion and a second portion.

A TOC of the first portion can be determined by a traditional method to determine a total TOC of the rock sample 101. This TOC of the first portion can be compared to a sum of the first level of TOC (determined at step 205) and the second level of TOC (determined at step 205').

The second portion can undergo a pre-processing step to remove contaminants. For example, the second portion can be solvent extracted. Then, a TOC of the second portion can be determined by a traditional method to determine a solvent extracted TOC of the rock sample 101. This TOC of the second portion can be compared to the second level of TOC (determined at step 205').

Figure 3:
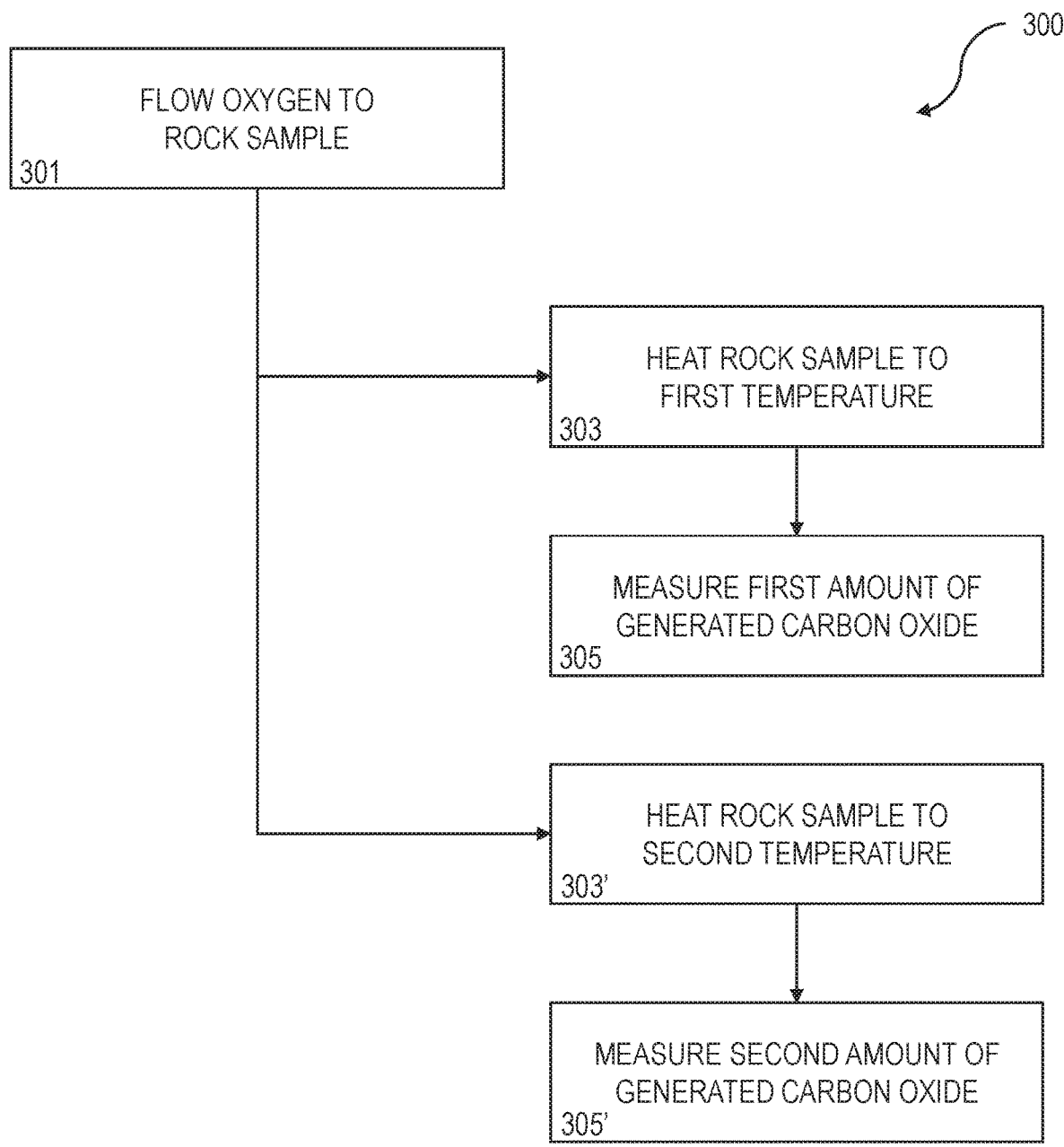
FIG. 3 is a flow chart of an example method for determining TOC of a rock sample.

FIG. 3 is a flow chart of an example method 300 for determining TOC of a rock sample (such as the rock sample 101). Method 300 is similar to method 200, and the chamber 150 can be used to implement method 300. At step 301, oxygen is flowed to the rock sample 101, which is obtained from a subterranean zone. Similar to step 201, oxygen can be flowed to the rock sample 101 at a rate in a range of from about 700 mL/min to about 750 mL/min (for example, 720 mL/min).

While flowing oxygen to the rock sample 101 at step 301, the rock sample 101 is heated to a first temperature at step 303 and then to a second temperature greater than the first temperature at step 303'. Heating the rock sample 101 to the first temperature at step 303 can cause a first portion of the rock sample 101 to oxidize, thereby generating a first amount of carbon oxide. In some implementations, the first temperature is in a range of from about 355° C. to about 365° C. (for example, approximately 360° C.). In some implementations, once the rock sample 101 is heated to the first temperature, the rock sample 101 is maintained at the first temperature for a time duration in a range of from about 1 minute to about 10 minutes (for example, approximately 2 minutes). In some implementations, the rock sample 101 is heated at step 303 such that the temperature of the rock sample 101 (or the inner volume of the chamber 150) increases at a rate in a range of from about 10° C./min to about 30° C./min (for example, approximately 15° C./min).

Heating the rock sample 101 to the second temperature at step 303' can cause a second portion of the rock sample 101 to oxidize, thereby generating a second amount of carbon oxide. In some implementations, the second temperature is in a range of from about 500° C. to about 650° C. (for example, approximately 600° C.). In some implementations, once the rock sample 101 is heated to the second temperature, the rock sample 101 is maintained at the second temperature for a time duration in a range of from about 30 seconds to about 8 minutes (for example, approximately 75 seconds). In some implementations, the rock sample 101 is heated at step 303' such that the temperature of the rock sample 101 (or the inner volume of the chamber 150) increases at a rate in a range of from about 25° C./min to about 50° C./min (for example, approximately 50° C./min).

At step 305, the first amount of generated carbon oxide is measured to determine a first level of TOC of the rock sample 101. The first level of TOC of the rock sample 101 can be attributed to contaminants that were present in the rock sample 101. The first amount of generated carbon oxide can be measured, for example, by using a nondispersive infrared (NDIR) sensor.

At step 305', the second amount of generated carbon oxide is measured to determine a second level of TOC of the rock sample 101. The second level of TOC of the rock sample 101 can be attributed to the native organic content that was already present in the rock sample 101 before the rock sample 101 was exposed to the contaminants (for example, during the drilling operations). The second amount of generated carbon oxide can be measured, for example, by using the NDIR sensor.

Example 1

Figure 4:
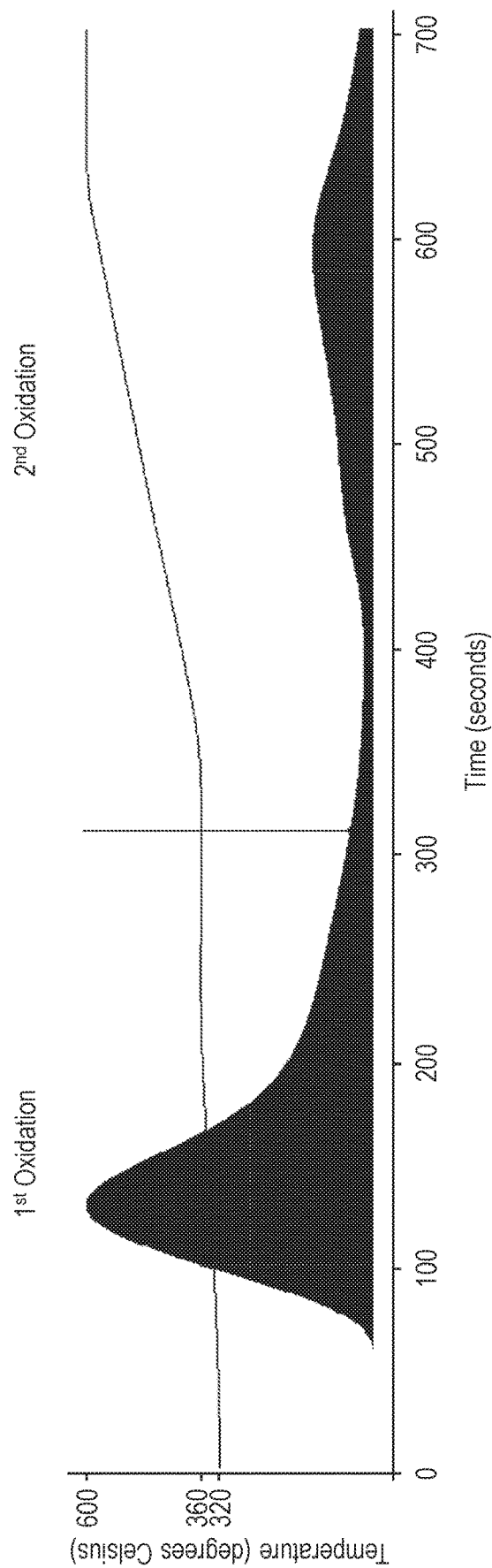
FIG. 4 is a thermal oxidation plot of a rock sample across two oxidation stages.

FIG. 4 is a plot of an example test run, for example, according to method 200 or method 300, for determining the TOC of an example rock sample. The rock sample was heated from 320° C. to 360° C. at a temperature increase rate of 10° C./min. The rock sample was maintained at 360° C. for 1 minute. The rock sample was then heated from 360° C. to 600° C. at a temperature increase rate of 45° C./min. The rock sample was maintained at 600° C. for 1 minute. The total oxidation process took approximately 12 minutes. The first "peak" of the shaded data curve represents the TOC measured for the first oxidation process (for example, the first heating process at step 203 or step 303). This first peak is attributable to contaminants present in the rock sample. The second peak of the shaded data curve represents the TOC measured for the second oxidation process (for example, the second heating process at step 203' or step 303'). This second peak is attributable to native organic content of the rock sample. The TOC levels were determined to be 2.84% for the first oxidation process and 1.24% for the second oxidation process (for a total TOC of 4.08%).

The same rock sample was also analyzed by a traditional method for comparison. For the traditional method, the TOC levels were determined to be 5.01% before solvent extraction (total TOC, including contaminants) and 1.27% after solvent extraction (native organic content, excluding contaminants). The 1.27% TOC level determined by the traditional method after solvent extraction is compared to the 1.24% TOC level of the second oxidation process (of the method described previously) because these values are attributable to the native organic content of the rock sample (excluding contaminants). In this particular example, the difference in total TOC measured by the two methods (4.08% by the method described previously, and 5.01% by the traditional method) can be attributed to the fact that the method described previously was performed some time after the traditional method, and contaminant evaporation could have occurred.

Example 2

The methods described previously (for example, method 200 and method 300) were compared with traditional methods to verify accuracy of measured TOC levels. 31 samples (including core and sidewall core samples) were obtained from various subterranean zones of varying maturities (from immature to over-mature) and varying lithology (including shale, sandstone, and carbonate). The samples had been exposed to contaminants from an oil based mud (OBM) having an oil-to-solids ratio (O/S) ranging from 50:50 to 80:20 or a water based mud, such as sodium chloride (NaCl) brine. Some of the samples were intentionally contaminated with an oil based mud with an oil-to-solids ratio of 70:30 (70:30 OBM). The level of intentional contamination by the 70:30 OBM ranged from 1% to 10% by weight of the sample. Carbonate content (which is considered an inorganic carbon) was determined for some of the samples using Rock-Eval 6 by Vinci Technologies. Table 1 shows some information about the 31 samples.

TABLE 1

| Sample Number | Carbonate Content (weight percent) | Drilling Fluid Type |
|---|---|---|
| 1 | 42.32 | 50:50 OBM |
| 2 | Not measured | 50:50 OBM |
| 3 | 6.97 | 50:50 OBM |
| 4 | 1.47 | 50:50 OBM |
| 5 | 4.35 | 68:32 OBM |
| 6 | 1.92 | 68:32 OBM |
| 7 | 0.63 | 68:32 OBM |
| 8* | 4.29 | 70:30 OBM |
| 9* | 5.24 | 70:30 OBM |
| 10* | 5.24 | 70:30 OBM |
| 11* | 5.24 | 70:30 OBM |
| 12* | 5.24 | 70:30 OBM |
| 13* | 10.44 | 70:30 OBM |
| 14* | 6.93 | 70:30 OBM |
| 15 | 8.94 | 80:20 OBM |
| 16 | 10.45 | 80:20 OBM |
| 17 | 12.58 | 80:20 OBM |
| 18 | Not measured | 80:20 OBM |
| 19 | Not measured | 80:20 OBM |
| 20 | 15.80 | 80:20 OBM |
| 21 | Not measured | 80:20 OBM |
| 22 | Not measured | NaCl Brine |

TABLE 1-continued

| Sample Number | Carbonate Content (weight percent) | Drilling Fluid Type |
|---|---|---|
| 23 | Not measured | NaCl Brine |
| 24 | Not measured | NaCl Brine |
| 25 | Not measured | NaCl Brine |
| 26 | Not measured | NaCl Brine |
| 27 | Not measured | NaCl Brine |
| 28 | Not measured | NaCl Brine |
| 29 | Not measured | NaCl Brine |
| 30 | 80.55 | NaCl Brine |
| 31 | 81.88 | NaCl Brine |

*Intentionally contaminated with 70:30 OBM.

Each of the samples were tested with a traditional method and a method according to this disclosure (for example, method 200 or method 300). For each of the samples, a first aliquot was tested with a traditional method to determine an original sample TOC. For each of the samples, a second aliquot was solvent extracted using dichloromethane and then tested with a traditional method to determine a solvent extracted TOC. For each of the samples, a second aliquot was tested with a method according to this disclosure. The sum of the TOCs determined from the $1^{st}$ oxidation process (step 203 or step 303) and the $2^{nd}$ oxidation process (step 203' or step 303') was the total oxidation TOC, which was analogous to the original sample TOC determined by the traditional method. The TOC determined from the $2^{nd}$ oxidation process (step 203' or step 303') was analogous to the solvent extracted TOC determined by the traditional method. For every 10 samples analyzed, a test run was performed on a standard with a known TOC to verify that the equipment was still working as expected.

Figure 5A:
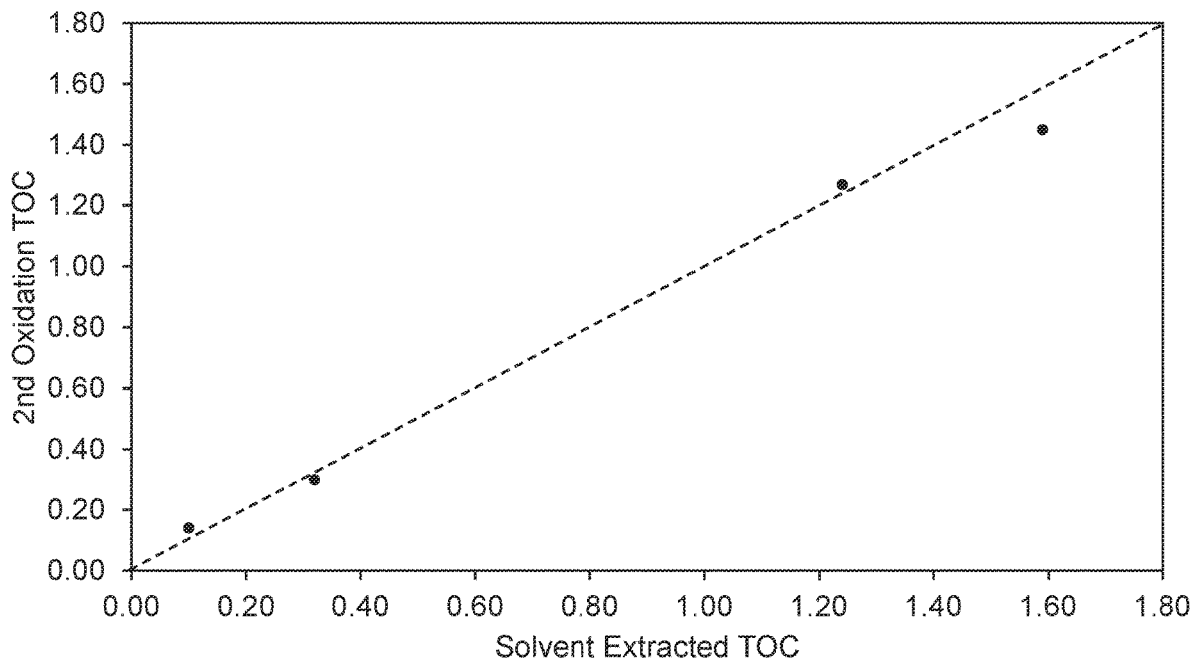
FIGS. 5A and 5B are plots of TOCs determined by two methods at various stages of rock samples that were exposed to a first drilling fluid.
Figure 5B:
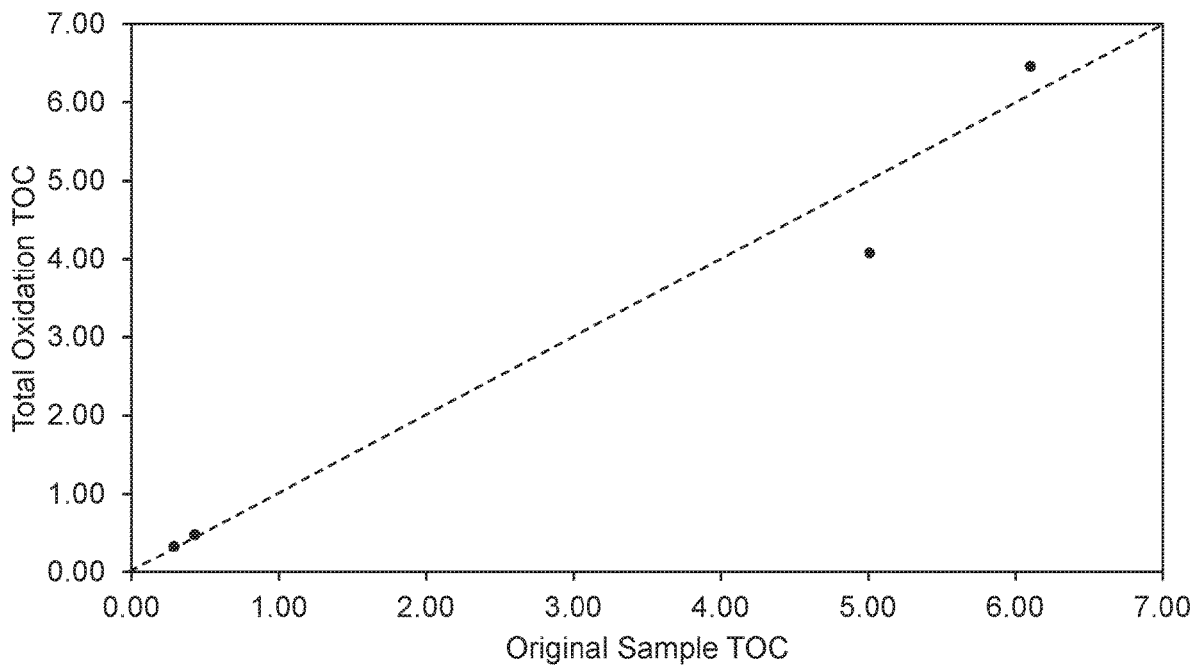

FIGS. 5A and 5B are related to the samples associated with the 50:50 OBM. FIG. 5A is a plot comparing the $2^{nd}$ oxidation TOC and the solvent extracted TOC. FIG. 5B is a plot comparing the total oxidation TOC and the original sample TOC. For each of these figures (and the following figures) a y=x line is provided as a dotted reference line because ideally, the $2^{nd}$ oxidation TOC and the solvent extracted TOC should be determined to be the same, and the total oxidation TOC and the original sample TOC should be determined to be the same.

Figure 6A:
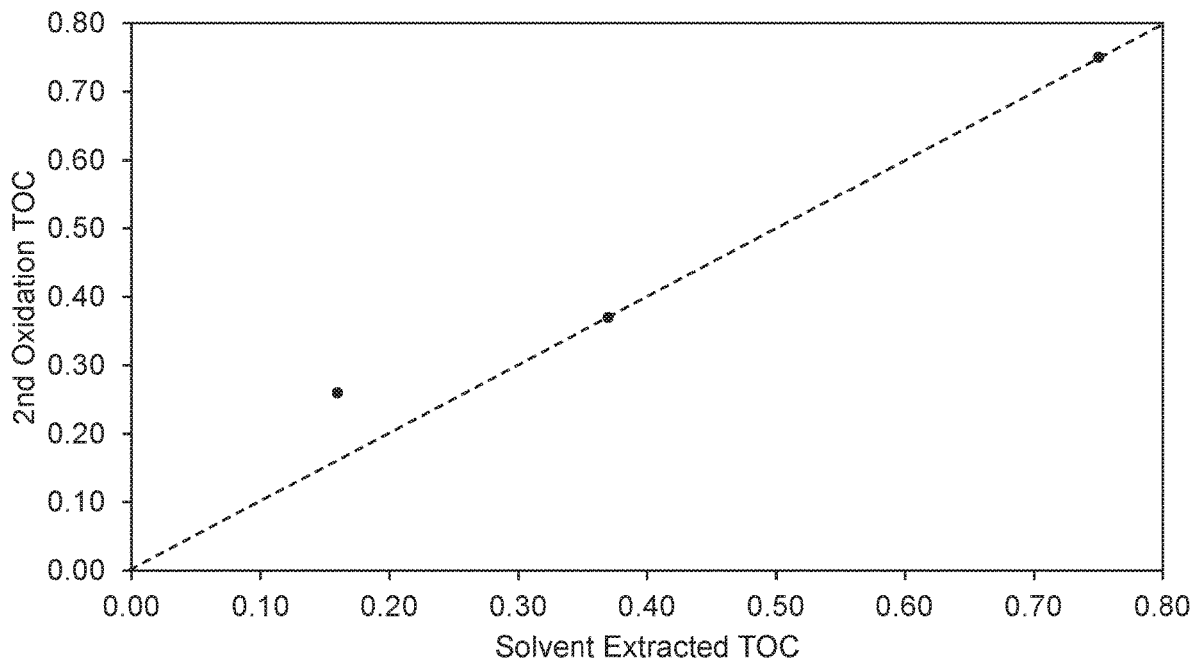
FIGS. 6A and 6B are plots of TOCs determined by two methods at various stages of rock samples that were exposed to a second drilling fluid.
Figure 6B:
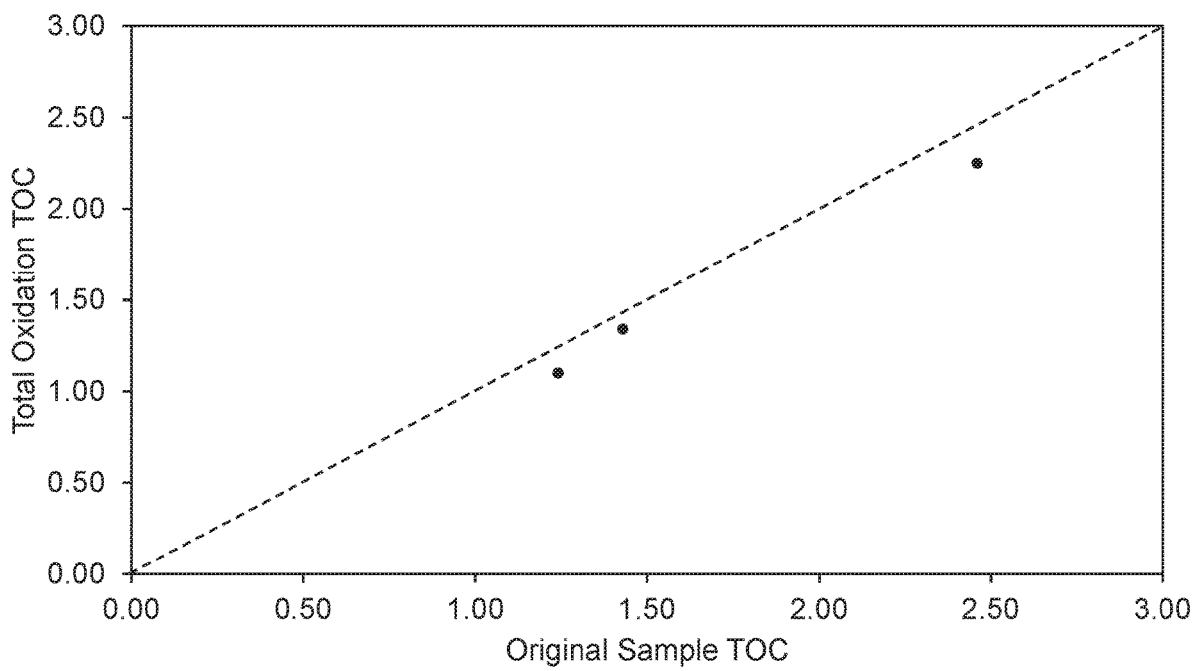

FIGS. 6A and 6B are related to the samples associated with the 68:32 OBM. FIG. 6A is a plot comparing the $2^{nd}$ oxidation TOC and the solvent extracted TOC. FIG. 6B is a plot comparing the total oxidation TOC and the original sample TOC.

Figure 7A:
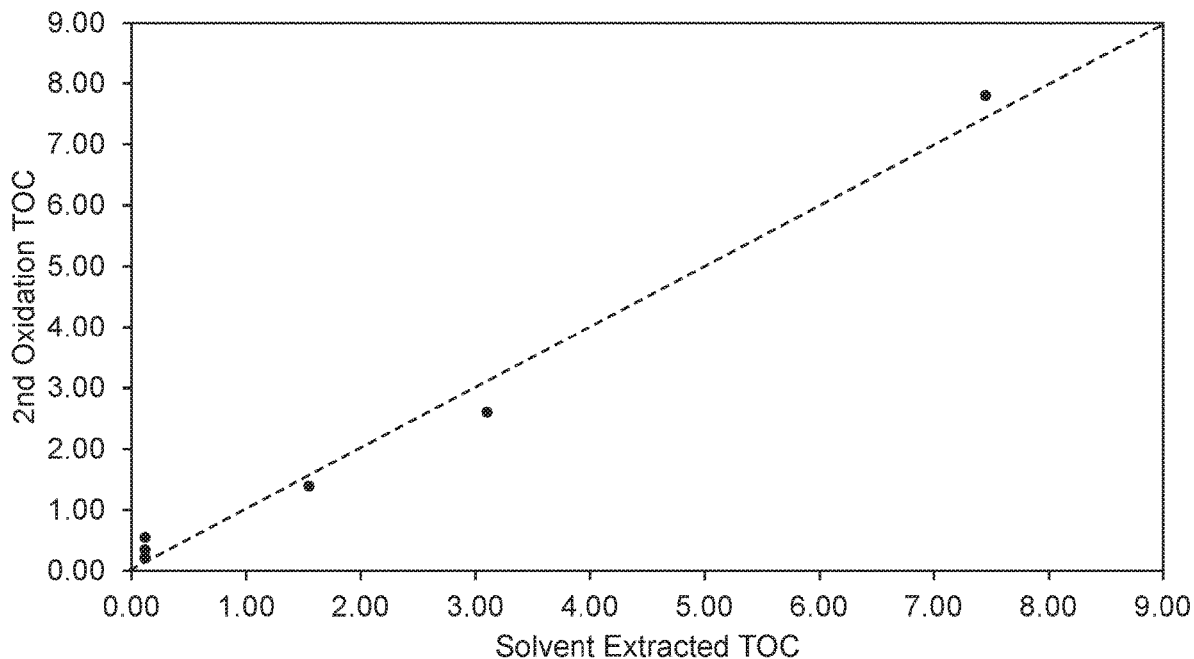
FIGS. 7A and 7B are plots of TOCs determined by two methods at various stages of rock samples that were exposed to a third drilling fluid.
Figure 7B:
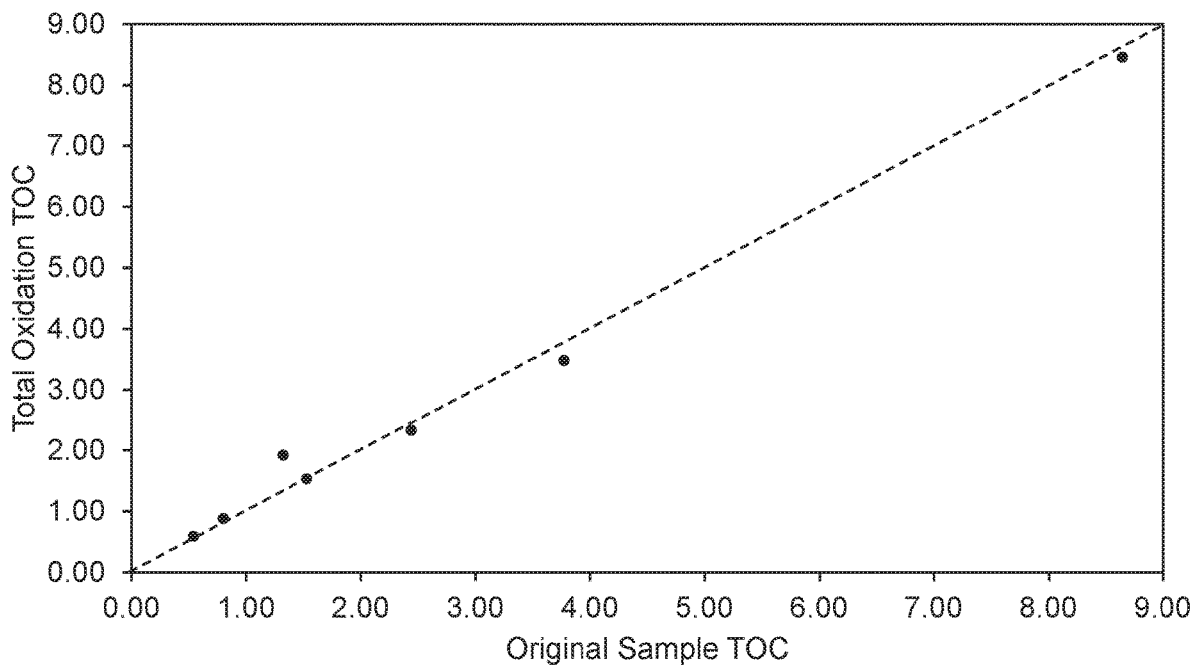

FIGS. 7A and 7B are related to the samples associated with the 70:30 OBM. FIG. 7A is a plot comparing the $2^{nd}$ oxidation TOC and the solvent extracted TOC. FIG. 7B is a plot comparing the total oxidation TOC and the original sample TOC.

Figure 8A:
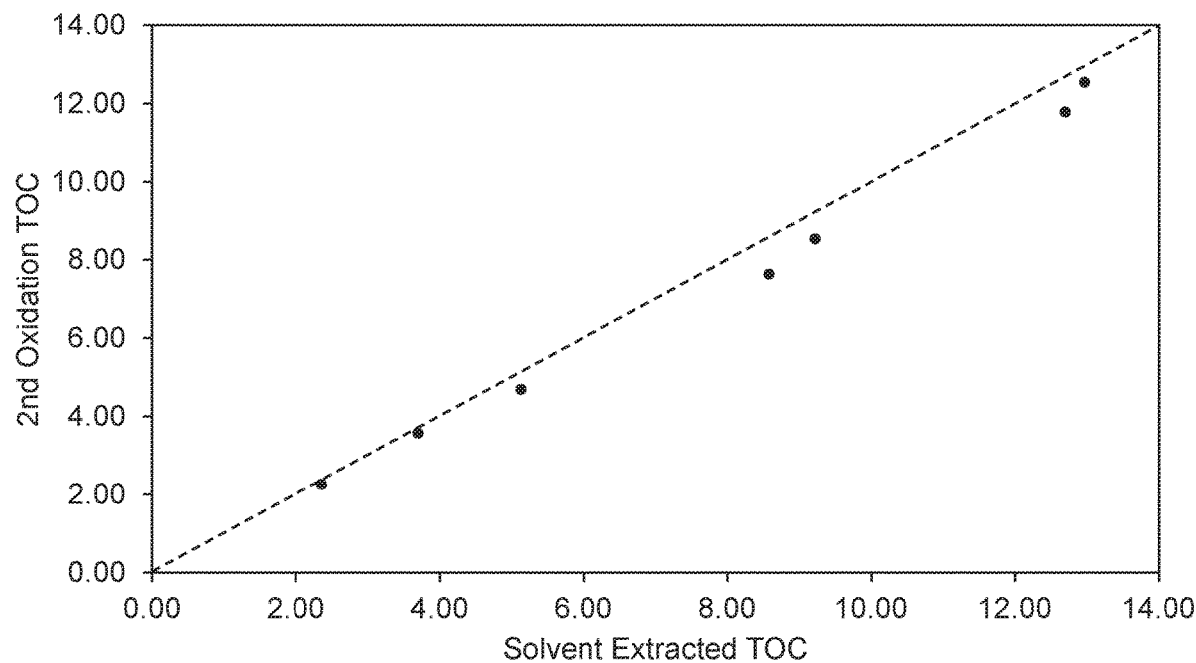
FIGS. 8A and 8B are plots of TOCs determined by two methods at various stages of rock samples that were exposed to a fourth drilling fluid.
Figure 8B:
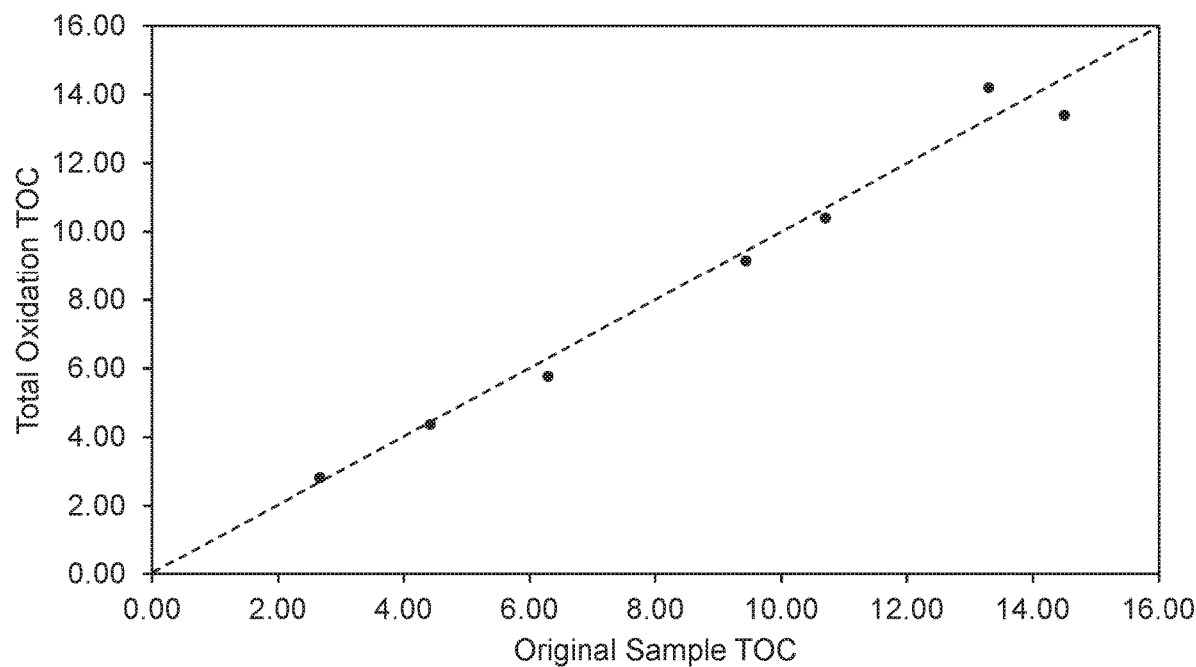

FIGS. 8A and 8B are related to the samples associated with the 80:20 OBM. FIG. 8A is a plot comparing the $2^{nd}$ oxidation TOC and the solvent extracted TOC. FIG. 8B is a plot comparing the total oxidation TOC and the original sample TOC.

Figure 9A:
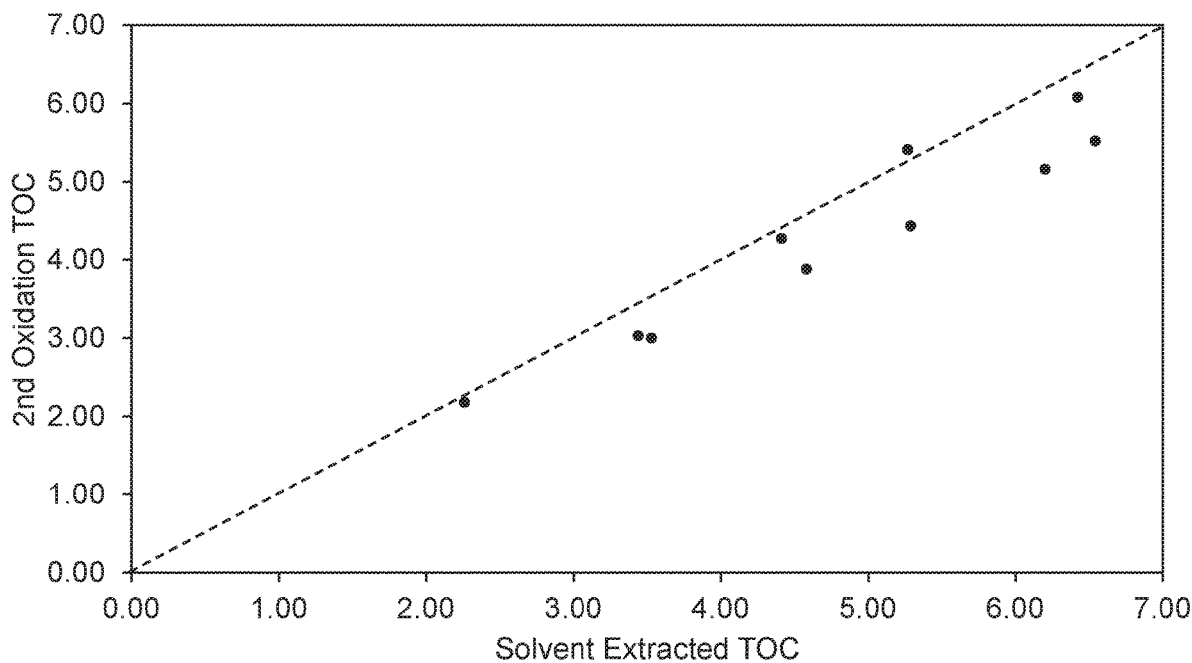
FIGS. 9A and 9B are plots of TOCs determined by two methods at various stages of rock samples that were exposed to a fifth drilling fluid.
Figure 9B:
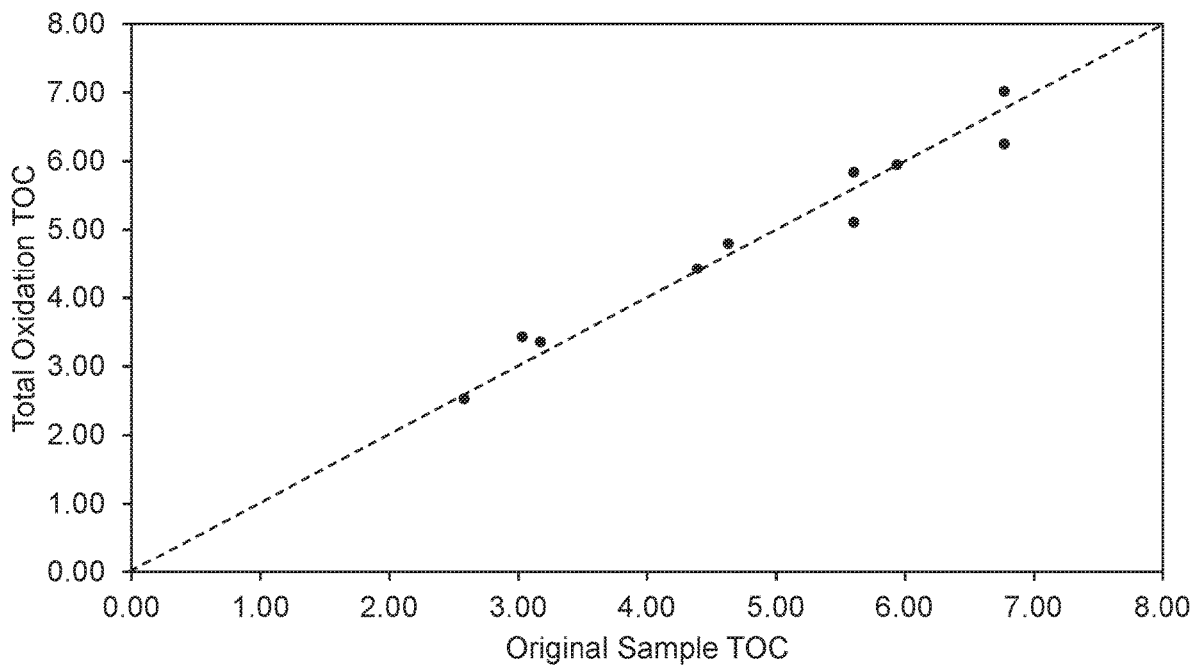

FIGS. 9A and 9B are related to the samples associated with the NaCl brine. FIG. 9A is a plot comparing the $2^{nd}$ oxidation TOC and the solvent extracted TOC. FIG. 9B is a plot comparing the total oxidation TOC and the original sample TOC.

Figure 10A:
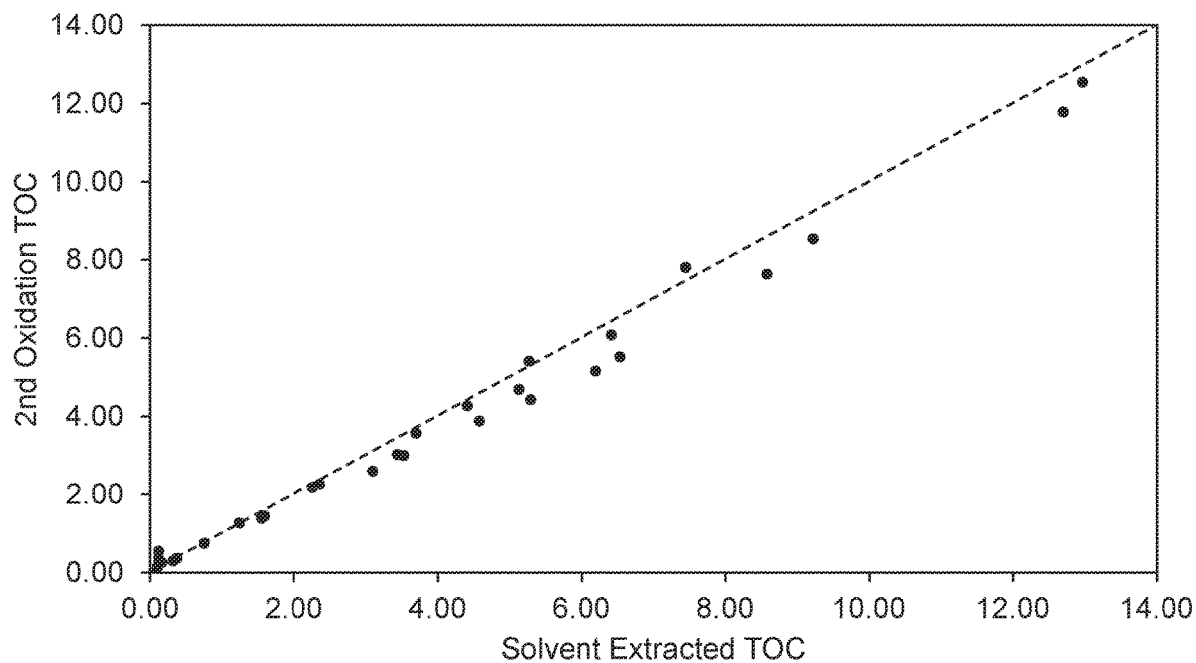
FIGS. 10A and 10B are combined plots of TOCs determined by two methods at various stages of the rock samples of FIGS. 5A, 5B, 6A, 6B, 7A, 7B, 8A, 8B, 9A, and 9B.
Figure 10B:
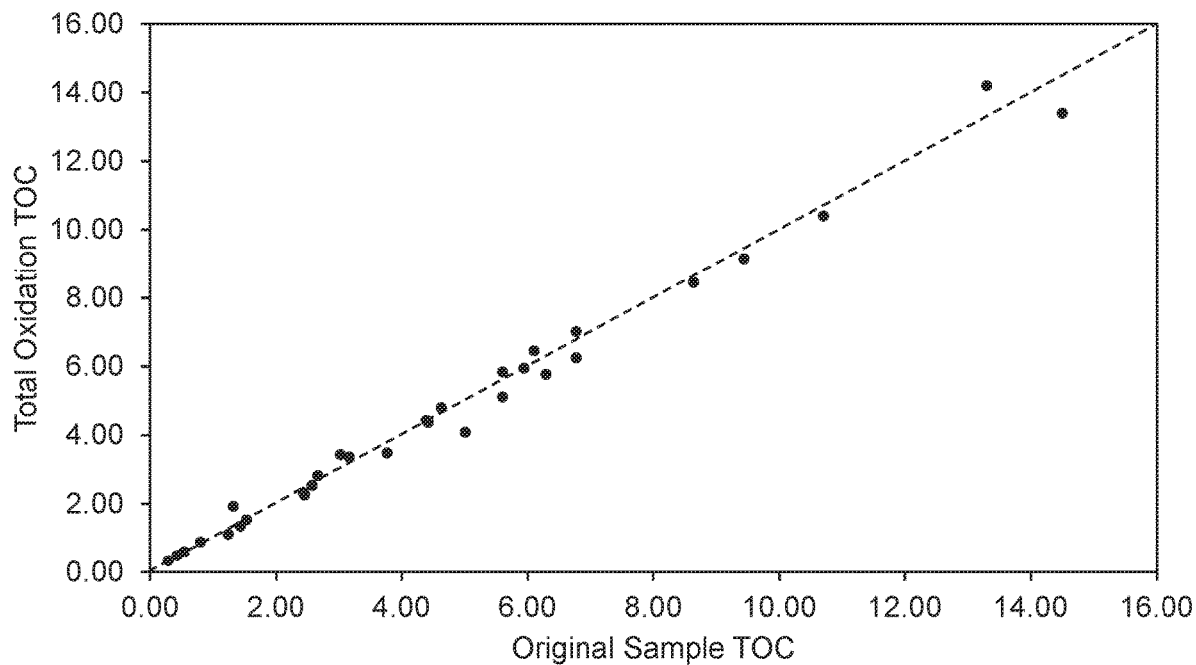

FIG. 10A is a combined plot comparing the $2^{nd}$ oxidation TOC and the solvent extracted TOC of all the samples. FIG. 10B is a combined plot comparing the total oxidation TOC and the original sample TOC of all the samples. The coefficient of determination ($r^2$) was calculated for the combined data of all the samples according to Equation 1:

$$r^2 \equiv 1 - \frac{SS_{res}}{SS_{tot}}, \quad (1)$$

where $SS_{res}$ is the residual sum of squares (Equation 2), and $SS_{tot}$ is the total sum of squares (Equation 3). The measured n data points ($y_1$ through $y_n$) are associated with "expected" n data points ($f_1$ through $f_n$). In this case, the measured data points can be considered the TOCs determined by one of the methods described previously, and the expected data points can be considered the TOCs determined by the traditional method. $SS_{res}$ can be calculated by Equation 2:

$$SS_{res} = \sum_{i=1}^{n} (y_i - f_i)^2 \quad (2)$$

$SS_{tot}$ can be calculated by Equation 3:

$$SS_{tot} = \sum_{i=1}^{n} (y_i - \bar{y})^2, \quad (3)$$

where $\bar{y}$ is the mean (also known as average) of the measured data points.

Referring to FIG. 10A, the comparison of the $2^{nd}$ oxidation TOC to the solvent extracted TOC of all the samples resulted in a $r^2$ value of 0.9536. Referring to FIG. 10B, the comparison of the total oxidation TOC to the original sample TOC of all the samples resulted in a $r^2$ value of 0.9762.

In this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

While this disclosure contains many specific implementation details, these should not be construed as limitations on the subject matter or on what may be claimed, but rather as descriptions of features that may be specific to particular implementations. Certain features that are described in this disclosure in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described.

Nevertheless, it will be understood that various modifications, substitutions, and alterations may be made. While operations are depicted in the drawings or claims in a particular order, this should not be understood as requiring that such operations be performed in the particular order shown or in sequential order, or that all illustrated operations be performed (some operations may be considered optional), to achieve desirable results. Accordingly, the previously described example implementations do not define or constrain this disclosure.

What is claimed is:

1. A method, comprising:
   providing a stream comprising oxygen to a rock sample from a subterranean zone, the rock sample comprising an organic material and a contaminant to which the rock sample was exposed during a drilling operation in the subterranean zone;
   while providing the stream to the rock sample,
   subjecting the rock sample to a first heating process to thermally oxidize at least a portion of the contaminant and generate a first amount of carbon oxide, the first heating process comprising:
   heating the rock sample to a first temperature greater than 320 degrees Celsius (° C.); and
   maintaining the rock sample at the first temperature for a first time duration; and
   subjecting the rock sample to a second heating process to thermally oxidize at least a portion of the organic material and generate a second amount of carbon oxide, the second heating process comprising:
   heating the rock sample to a second temperature greater than 360° C., the second temperature different from the first temperature; and
   maintaining the rock sample at the second temperature for a second time duration;
   determining a first level of total organic content (TOC) of the rock sample based on the first amount of generated carbon oxide resulting from subjecting the rock sample to the first heating process; and
   determining a second level of TOC of the rock sample based on the second amount of generated carbon oxide resulting from subjecting the rock sample to the second heating process.

2. The method of claim 1, comprising heating the rock sample to approximately 320° C. before subjecting the rock sample to the first heating process.

3. The method of claim 2, wherein the first temperature is approximately 360° C., and the first time duration is approximately 2 minutes.

4. The method of claim 3, wherein the second temperature is approximately 600° C., and the second time duration is approximately 75 seconds.

5. The method of claim 4, wherein heating the rock sample to the second temperature comprises heating the rock sample such that the temperature of the rock sample increases at a rate of approximately 50° C. per minute.

6. The method of claim 3, wherein heating the rock sample to the first temperature comprises heating the rock sample such that the temperature of the rock sample increases at a rate of approximately 15° C. per minute.

7. The method of claim 1, comprising grinding the rock sample before providing the stream to the rock sample.

8. The method of claim 7, wherein grinding the rock sample comprises grinding the rock sample such that the resulting ground rock sample has an average particle size of at most 250 micrometers.

9. The method of claim 7, comprising:
reserving a portion of the ground rock sample before providing the stream to a remaining portion of the ground rock sample;
separating the reserved portion of the ground rock sample into a first portion and a second portion;
determining a TOC of the first portion;
removing at least a portion of the contaminant from the second portion with a solvent; and
after removing the contaminant from the second portion, determining a TOC of the second portion.

10. The method of claim 9, comprising verifying the accuracy of the determination of the first and second levels of TOC by:
comparing the TOC of the first portion to a sum of the first level of TOC and the second level of TOC; and
comparing the TOC of the second portion to the second level of TOC.

11. The method of claim 1, wherein determining the first level of TOC of the rock sample comprises measuring the first amount of generated carbon oxide, and determining the second level of TOC of the rock sample comprises measuring the second amount of generated carbon oxide.

12. The method of claim 1, wherein providing the stream to the rock sample comprises providing oxygen at a rate of approximately 720 milliliters per minute to the rock sample.

13. The method of claim 12, wherein the stream comprises at least 99% by volume of oxygen.

14. A method, comprising:
flowing oxygen to a rock sample obtained from a subterranean zone;
while flowing oxygen to the rock sample,
heating the rock sample to a first temperature to thermally oxidize a first portion of the rock sample, thereby generating a first amount of carbon oxide, wherein heating the rock sample to the first temperature comprises heating the rock sample such that the temperature of the rock sample increases at a rate of approximately 15° C. per minute until the temperature of the rock sample reaches approximately 360° C.;
after heating the rock sample to the first temperature, heating the rock sample to a second temperature greater than the first temperature to thermally oxidize a second portion of the rock sample, thereby generating a second amount of carbon oxide;
measuring the first amount of generated carbon oxide to determine a first level of total organic content (TOC) of the rock sample; and
measuring the second amount of generated carbon oxide to determine a second level of TOC of the rock sample.

15. The method of claim 14, comprising maintaining the rock sample at approximately 360° C. for approximately 2 minutes once the temperature of the rock sample reaches approximately 360° C., before heating the rock sample to the second temperature.

16. The method of claim 14, wherein heating the rock sample to the second temperature comprises heating the rock sample such that the temperature of the rock sample increases at a rate of approximately 50° C. per minute until the temperature of the rock sample reaches approximately 600° C.

17. The method of claim 16, comprising maintaining the rock sample at approximately 600° C. for approximately 75 seconds once the temperature of the rock sample reaches approximately 600° C.

18. The method of claim 14, wherein measuring the first and second amounts of generated carbon oxide comprises using a nondispersive infrared (NDIR) sensor.

19. The method of claim 14, wherein flowing oxygen to the rock sample comprises flowing oxygen to the rock sample at a rate of approximately 720 milliliters per minute.

* * * * *